(12) United States Patent
Farmer et al.

(10) Patent No.: US 11,788,054 B2
(45) Date of Patent: Oct. 17, 2023

(54) METHODS FOR PRODUCTION OF MANNOSYLERYTHRITOL LIPIDS

(71) Applicant: Locus Solutions IPCo, LLC, Solon, OH (US)

(72) Inventors: Sean Farmer, Ft. Lauderdale, FL (US); Ken Alibek, Solon, OH (US); Blake Ott, Solon, OH (US)

(73) Assignee: Locus Solutions IPCo, LLC, Solon, OH (US)

( * ) Notice: Subject to any disclaimer, the term of this patent is extended or adjusted under 35 U.S.C. 154(b) by 221 days.

(21) Appl. No.: 17/429,773

(22) PCT Filed: Feb. 21, 2020

(86) PCT No.: PCT/US2020/019241
§ 371 (c)(1),
(2) Date: Aug. 10, 2021

(87) PCT Pub. No.: WO2020/172543
PCT Pub. Date: Aug. 27, 2020

(65) Prior Publication Data
US 2022/0127563 A1    Apr. 28, 2022

Related U.S. Application Data

(60) Provisional application No. 62/808,398, filed on Feb. 21, 2019.

(51) Int. Cl.
*C12P 7/64* (2022.01)
*C12N 1/16* (2006.01)
*C12P 19/44* (2006.01)

(52) U.S. Cl.
CPC ............... *C12N 1/16* (2013.01); *C12P 19/44* (2013.01)

(58) Field of Classification Search
CPC .... C12P 7/64; C12P 19/44; C12N 1/16; Y02P 20/582
See application file for complete search history.

(56) References Cited

U.S. PATENT DOCUMENTS

2016/0083757 A1* 3/2016 Fonseca et al. .......... C12P 7/64

FOREIGN PATENT DOCUMENTS

| WO | 2018148265 A2 | 8/2018 |
| WO | 2018208530 A1 | 11/2018 |

OTHER PUBLICATIONS

Faria N.T. et al., "Production of glycolipid biosurfactants, mannosylerythritol lipids, from pentoses and d-glucose/d-xylose mixtures by Pseudozyma yeast strains", Process Biochemistry, 2014, vol. 49, pp. 1790-1799. (Year: 2014).*

Camargo, F. P., et al., "Characterization of Biosurfactant from Yeast Using Residual Soybean Oil Under Acidic Conditions and their Use in Metal Removal Processes." FEMS Microbiology Letters, 2018, 365(10): 1-8.

Joaad, A. I. M., et al., "Effect of Different Environmental and Nutritional Factors on Biosurfactant Production from Candida guilliermondii." Iraqi Journal of Science, 2015, 56(1B): 329-336.

Kaur, K., et al., "Biosurfactant Production by Yeasts Isolated from Hydrocarbon Polluted Environments." Environ. Monit. Assess, 2017, 189(603): 1-13.

* cited by examiner

*Primary Examiner* — Satyendra K Singh
(74) *Attorney, Agent, or Firm* — SALIWANCHIK, LLOYD & EISENSCHENK

(57) ABSTRACT

The subject invention provides improved methods for producing mannosylerythritol lipids (MEL) using yeasts not previously known to produce MEL. In particular, *Meyerozyma guilliermondii* (*Pichia guilliermondii*) is cultivated in a specially-tailored nutrient medium and under cultivation conditions such that the yeast unnaturally produces MEL and/or MEL-like molecules in greater amounts and at increased rates than when using standard MEL production with, for example, *Pseudozyma aphidis*. Yeast culture compositions are also provided, comprising yeast cells, growth medium, and high concentrations of MEL.

13 Claims, 7 Drawing Sheets

METHODS FOR PRODUCTION OF MANNOSYLERYTHRITOL LIPIDS

CROSS-REFERENCE TO RELATED APPLICATION

This application is a National Stage Application of International Application No. PCT/US2020/019241. filed Feb. 21, 2020; which claims priority to U.S. Provisional Patent Application No. 62/808,398, filed Feb. 21, 2019, both of which are incorporated herein by reference in their entirety.

BACKGROUND OF THE INVENTION

Microorganisms, such as yeast, fungi and bacteria, are important for the production of a wide variety of bio-preparations that are useful in many settings, such as oil production; agriculture; remediation of soils, water and other natural resources; mining; animal feed; waste treatment and disposal; food and beverage preparation and processing; and human health.

Interest in microbial surfactants, in particular, has been steadily increasing in recent years due to their diversity, environmentally friendly nature, selectivity, performance under extreme conditions, and potential applications in environmental protection. Microbially produced surfactants, i.e., biosurfactants, are amphiphiles. They consist of two parts: a polar (hydrophilic) moiety and non-polar (hydrophobic) group. Due to their amphiphilic structure, biosurfactants reduce the surface and interfacial tensions between the molecules of liquids, solids, and gases.

Additionally, biosurfactants accumulate at interfaces, thus leading to the formation of aggregated micellar structures in solution. The ability of biosurfactants to form pores and destabilize biological membranes permits their use as, e.g., antibacterial and antifungal agents. Furthermore, biosurfactants are biodegradable, have low toxicity, and can be produced using low-cost renewable resources. They can inhibit microbial adhesion to a variety of surfaces, prevent the formation of biofilms, and can have powerful emulsifying and demulsifying properties.

Combined with the characteristics of low toxicity and biodegradability, biosurfactants can be useful in a variety of settings and industries. Most biosurfactant-producing organisms produce biosurfactants in response to the presence of a hydrocarbon source in the growing media. Other media components, such as concentration of minerals and pH, can also affect biosurfactant production significantly.

Microbial biosurfactants are produced by a variety of microorganisms such as bacteria, fungi, and yeasts, including, for example, *Starmerella* spp. (e.g., *S. bombicola*), *Pseudomonas* spp. (e.g., *P. aeruginosa, P. putida, P. florescens, P. fragi, P. syringae*); *Flavobacterium* spp.; *Bacillus* spp. (e.g., *B. subtilis, B. amyloliquefaciens, B. pumillus, B. cereus, B. licheniformis*); *Wickerhamomyces* spp. (e.g., *W. anomalus*), *Candida* spp. (e.g., *C. albicans, C. rugosa, C. tropicalis, C. lipolytica, C. torulopsis*); *Saccharomyces* (e.g., *S. cerevisiae*); *Pseudozyma* spp. (e.g., *P. aphidis*); *Rhodococcus* spp. (e.g., *R. erythropolis*); *Ustilago* spp.; *Arthrobacter* spp.; *Campylobacter* spp.; *Corynebacterium* spp.; as well as others.

Biosurfactants can include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

One important type of biosurfactant is mannosylerythritol lipids (MEL). MEL are glycolipid, with properties including, for example, viscosity reduction, emulsification, and nematode control. MEL and MEL-like substances are produced mainly by *Pseudozyma* spp., but some are also produced by *Ustilago* spp. (Arutchelvi et al., 2008).

MEL can be produced in more than 93 different combinations that fall under 5 main categories: MEL A, MEL B, MEL D, Tri-acetylated MEL A, and Tri-acetylated MEL B/C. Current production techniques take 10 to 14 days for accumulation of MEL using *P. aphidis*. The product then needs to be extracted using potentially harmful solvents and concentrated using a labor-intensive process.

Two principle forms of microbe cultivation exist for growing microbes and producing their growth by-products: submerged (liquid fermentation) and surface cultivation (solid-state fermentation (SSF)). Both cultivation methods require a nutrient medium for the growth of the microorganisms, and are classified based on the type of substrate used during fermentation (either a liquid or a solid substrate). The nutrient medium for both types of fermentation typically includes a carbon source, a nitrogen source, salts and other appropriate additional nutrients and microelements.

In particular, SSF utilizes solid substrates, such as bran, bagasse, and paper pulp, for culturing microorganisms. One advantage to this method is that nutrient-rich waste materials can be easily recycled as substrates. Additionally, the substrates are utilized very slowly and steadily, so the same substrate can be used for long fermentation periods; however, this method is not always ideal when higher culture turnover rate is desired.

Submerged fermentation utilizes free flowing liquid substrates, such as molasses and nutrient broth, into which bioactive compounds are secreted by the growing microbes. Submerged cultivation can be achieved relatively quickly, but the substrates are utilized quite rapidly, thus requiring constant replenishment and/or supplementation with nutrients.

Microbes and their growth by-products have the potential to play highly beneficial roles in, for example, the oil and agriculture industries; however, more efficient methods are needed for producing the large quantities of microbe-based products, such as MEL and MEL-like substances, that are required for such applications.

BRIEF SUMMARY OF THE INVENTION

The subject invention provides materials and methods for the efficient production and use of beneficial microbes, as well as for the production and use of substances, such as metabolites, derived from these microbes and the substrate in which they are produced.

In particular, the subject invention provides materials and methods for producing mannosylerythritol lipids (MEL). Advantageously, the subject invention increases efficiency and reduces costs associated with MEL production, compared to traditional production methods.

In general, the subject methods involve cultivating a yeast strain under specially-tailored conditions, wherein these conditions influence one or more biological mechanisms, which, when activated in the yeast, result in the unnatural production of the desired growth by-product(s) (e.g., MEL). In certain embodiments, the one or more biological mechanisms are inactive or weakly active in the yeast, absent these influencing conditions.

In specific embodiments, the methods utilize the yeast *Meyerozyma guilliermondii*, also known as *Pichia guilliermondii*. *M. guilliermondii* was previously not known to possess the biological mechanism(s) and/or capability for producing MEL; thus, the methods of the subject invention provide for the unexpected and advantageous result of non-natural MEL production. Furthermore, the subject methods lead to production of surprisingly higher MEL yields than are achieved when cultivating *Pseudozyma* and/or *Ustilago*, and in less time.

In certain specific embodiments, the method comprises two phases: 1) biomass accumulation and 2) MEL production.

In one embodiment, phase one of the method comprises inoculating an initial nutrient medium with a *Meyerozyma guilliermondii* yeast to produce a yeast culture; and cultivating the yeast culture for 1-7 days, e.g., 2 days, at a temperature and at a pH favorable for accumulation of yeast cell biomass.

In certain embodiments, the initial nutrient medium comprises glucose and sources of proteins, amino acids, nitrogen, potassium, phosphorous, magnesium, calcium, sodium, and/or carbon.

In an exemplary embodiment, the initial nutrient medium comprises glucose, ammonium nitrate, potassium phosphate, monosodium phosphate, magnesium sulfate heptahydrate, magnesium sulfate monohydrate, and calcium chloride monohydrate.

In certain embodiments, the nutrient medium in phase one further comprises one or both of soybean oil and mannose.

In one embodiment, the temperature favorable for accumulation of yeast biomass is about 25° C. to 30° C. In a specific embodiment, the temperature is about 26° C. to 28° C.

In one embodiment, the pH favorable for accumulation of yeast biomass is about 5.5 to 7.0. In a specific embodiment, the pH is about 6.0 to 6.5.

In one embodiment, phase two of the method comprises altering the initial nutrient medium, cultivation temperature and cultivation pH, and continuing to cultivate the yeast culture for 1 to 7 additional days. In certain embodiments, the alterations in nutrient medium, temperature and pH influence the yeast to produce MEL in the culture.

In one embodiment, altering the initial nutrient medium comprises supplementing the nutrient medium with a sugar alcohol and/or mannose, and/or replacing the glucose with a source of fatty acids. In certain embodiments, the source of fatty acids is an oil, such as, for example, soybean oil, canola oil, safflower oil, olive oil, corn oil, rapeseed oil, peanut oil, or another vegetable or plant-based oil.

In one embodiment, the cultivation temperature is lowered to about 23° C. to 25° C. (e.g., about 24° C.) during phase two of the subject methods.

In one embodiment, the cultivation pH is lowered to about 3.5 to 4.0. In certain embodiments, the pH naturally lowers during the course of cultivation. Thus, in some embodiments, the method can comprise simply stabilizing the pH upon reaching 3.5 to 4.0.

After continuing to cultivate the yeast culture, for example, for an additional 1 to 7 days, or an additional 1 to 5 days (after phase one), MEL production can be observed. In certain embodiments, MEL production is observed after as little as 24 hours after the start of phase two.

According to the subject methods, the MEL growth by-products can be retained in the cells of the microorganisms and/or secreted into the solid substrate and/or liquid medium in which the microbes are growing. In preferred embodiments, the MEL by-products are produced into the culture, where they separate into a foamy layer at the top of the culture. Advantageously, this stratification allows for improved, safer recovery of the MEL product, compared with solvent extraction methods. In some embodiments, the MEL can be recovered from the culture simply by hand and/or by mechanical collection of the foam, and, if desired, can be purified according to known methods.

The subject methods can be useful for producing MEL, including MEL subtypes, isoforms, and isomers, as well as MEL-like molecules. In certain embodiments, a plurality of these molecules, in any combination, can be recovered from one *M. guilliermondii* culture produced according to the subject methods.

In certain embodiments, the methods of the subject invention comprise cultivating a microorganism and/or a microbial growth by-product using solid state fermentation (SSF), submerged fermentation, or modified versions and/or combinations thereof. Furthermore, the method can comprise aerobic and/or anaerobic fermentation.

The methods can be scaled up or down in size. Most notably, the methods can be scaled to an industrial scale, i.e., a scale that is suitable for use in supplying MEL and MEL-like substances in amounts to meet the demand for commercial applications, for example, mass-production of cosmetics.

In certain embodiments, the subject invention provides microbe-based products, as well as their uses in a variety of settings including, for example, oil and gas production; bioremediation and mining; waste disposal and treatment; animal health (e.g., livestock production and aquaculture); plant health and productivity (e.g., agriculture, horticulture, crops, pest control, forestry, turf management, and pastures); and human health (e.g., probiotics, pharmaceuticals and cosmetics).

The microbe-based products can comprise the entire culture produced according to the subject methods, including the microorganisms and/or their growth by-products, as well as residual growth medium and/or nutrients. The microorganisms can be live, viable or in an inactive form. They can be in the form of a biofilm, vegetative cells, spores, conidia, hyphae, mycelia and/or a combination thereof. In certain embodiments, no microbes are present, wherein the composition comprises microbial growth by-products, e.g., MEL, that have been extracted from the culture and, optionally, purified.

DETAILED DESCRIPTION

Figure 1A:
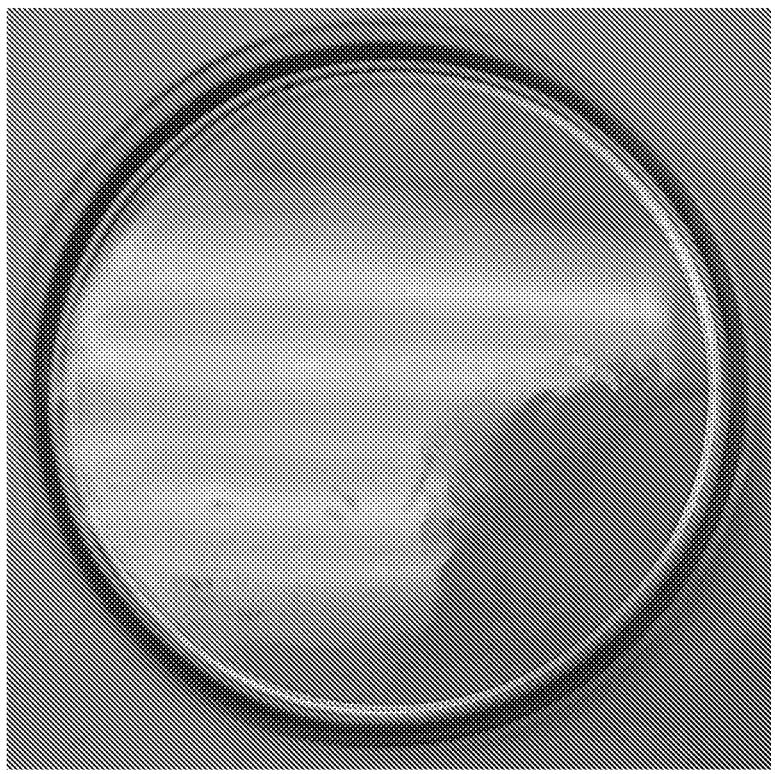
FIGS. 1A-1B show the results of an oil displacement test conducted using purified MEL from *M. guilliermondii* culture produced according to an embodiment of the subject invention. 1A shows a petri dish containing oil prior to being treated, and 1B shows the same petri dish comprising displaced oil after treatment with the *M. guilliermondii* MEL product.

The subject invention provides materials and methods for producing mannosylerythritol lipids (MEL). Advantageously, the subject invention increases efficiency and reduces costs associated with MEL production, compared to traditional production methods.

In general, the subject methods involve cultivating a yeast strain under specially-tailored conditions, wherein these conditions influence one or more biological mechanisms, which, when activated in the yeast, result in the unnatural production of the desired growth by-product(s) (e.g., MEL). In certain embodiments, the one or more biological mechanisms are inactive or weakly active in the yeast, absent these influencing conditions.

In specific embodiments, the methods utilize the yeast *Meyerozyma guilliermondii*, also known as *Pichia guilliermondii*. Advantageously, the subject methods lead to surprisingly higher MEL yields than is achieved when cultivating *Pseudozyma* and/or *Ustilago*, and in less time.

Selected Definitions

As used herein, a "biofilm" is a complex aggregate of microorganisms, wherein the cells adhere to each other and produce extracellular substances that encase the cells. Biofilms can also adhere to surfaces. The cells in biofilms are physiologically distinct from planktonic cells of the same organism, which are single cells that can float or swim in liquid medium.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. An isolated microbial strain means that the strain is removed from the environment in which it exists in nature. Thus, the isolated strain may exist as, for example, a biologically pure culture, or as spores (or other forms of propagule) in association with a carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, an "isomer" refers to a molecule with an identical chemical formula to another molecule, but having unique structures. Isomers can be constitutional isomers, where atoms and functional groups are bonded at different locations, and stereoisomers (spatial isomers), where the bond structure is the same but the geometrical positioning of atoms and functional groups in space is different. MEL isomers, for example, can differ in bond type and bond location of the carbohydrate, fatty acid and/or acetyl groups.

In contrast, an "analog" of a molecule does not have an identical chemical formula, but can have similar structure and/or functions. A "structural analog" or "chemical analog" is a compound having a structure that is similar to that of another compound, but having one or more differing components, such as one or more different atoms, functional groups, or substructures. As used herein, "functional analogs," are compounds that have similar physical, chemical, biochemical, or pharmacological properties. Despite their similarities, however, chemical analogs can be, but are not always, functional analogs, and functional analogs can be, but are not always, chemical analogs.

A "metabolite" refers to any substance produced by metabolism (e.g., a growth by-product) or a substance necessary for taking part in a particular metabolic process. A metabolite can be an organic compound that is a starting material, an intermediate in, or an end product of metabolism. Examples of a metabolite include, but are not limited to, biosurfactants, enzymes, biopolymers, bioemulsifiers, acids, solvents, amino acids, nucleic acids, peptides, proteins, lipids, carbohydrates, vitamins and/or minerals.

The systems and methods of the subject invention can be used to produce microbe-based compositions. As used herein, a "microbe-based composition" is a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, proteins, and/or other cellular components. The microbes may be intact or lysed. In some embodiments, the microbes are present, with medium in which they were grown, in the microbe-based composition. The cells may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more cells per gram or milliliter of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise only a portion of the product of cultivation (e.g., only the growth by-products), and/or the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as amino acids, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein "reduction" means a negative alteration, and "increase" means a positive alteration, wherein the negative or positive alteration is at least 1%, 5%, 10%, 25%, 50%, 75%, or 100%.

As used herein, "surfactant" means a surface-active compound that lower the surface tension (or interfacial tension) between two liquids or between a liquid and a solid. Surfactants act as, e.g., detergents, wetting agents, emulsifiers, foaming agents, and dispersants. A "biosurfactant" is a surface-active substance produced by a living cell.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Methods for Producing MEL

The subject invention provides methods for cultivation of microorganisms and production of microbial metabolites and/or other by-products of microbial growth using solid state fermentation, submerged fermentation, or a combination thereof. As used herein "fermentation" refers to growth of cells under controlled conditions. The growth could be aerobic or anaerobic.

In particular, the subject invention provides materials and methods for producing mannosylerythritol lipids (MEL), wherein a yeast strain is cultivated under specially-tailored conditions that influence one or more biological mechanisms, which, when activated in the yeast, result in unnatural production of the desired growth by-product(s) (e.g., MEL).

In certain embodiments, the one or more biological mechanisms are inactive or weakly active in the yeast, absent these influencing conditions.

In specific embodiments, the methods utilize the yeast *Meyerozyma guilliermondii*, also known as *Pichia guilliermondii*. *M. guilliermondii* was previously not known to possess the biological mechanism(s) and/or capability for producing MEL; thus, the methods of the subject invention provide for the unexpected and advantageous result of non-natural MEL production. Furthermore, the subject methods lead to surprisingly higher MEL yields than are achieved when cultivating *Pseudozyma* and/or *Ustilago*, and in less time.

In certain specific embodiments, the method comprises two phases: 1) biomass accumulation and 2) MEL production.

As used, herein, a "MEL" refers to a biosurfactant comprising either 4-O—B-D-mannopyranosyl-meso-erythritol or 1-O—B-D-mannopyranosyl-meso-erythritol as the hydrophilic moiety, and fatty acid groups and/or acetyl groups as the hydrophobic moiety. Isomers and/or analogs thereof are also included. For example, MEL isomers can differ in bond type and bond location of the carbohydrate, fatty acid and/or acetyl groups.

"MEL" can also include MEL molecules that have been modified, either synthetically or in nature. For example, MEL can comprise different carbon-length chains or different numbers of acetyl and/or fatty acid groups. MEL and/or modified forms thereof according to the subject invention can include, for example, tri-acylated, di-acylated, mono-acylated, tri-acetylated, di-acetylated, mono-acetylated and non-acetylated MEL, as well as stereoisomers and/or constitutional isomers thereof. Furthermore, there can be one to three esterified fatty acids, from 6 to 12 carbons, or more, in chain length.

"MEL" can also include "MEL-like" molecules, which are amphiphilic molecules that comprise the general glycolipid structure and/or that structurally and/or functionally exhibit similarities to known MEL molecules. The general structure of a glycolipid comprises a mono- or oligosaccharide group attached to a sphingolipid or a glycerol group that can be acetylated or alkylated, and one or more fatty acids. MEL-like molecules can include, for example, mannose-based amphiphilic molecules, fatty acid esters, and/or any isomer or analog of a molecule within these categories.

In certain specific embodiments, the MEL are selected from members of the following groups: MEL A (di-acetylated), MEL B (mono-acetylated at C4), MEL C (mono-acetylated at C6), MEL D (non-acetylated), tri-acetylated MEL A, tri-acetylated MEL B/C, and further including all possible isomers of the members of these groups.

In certain embodiments, the MEL are MEL-like molecules characterized as fatty acid esters. The fatty acid chain(s) of the fatty acid esters can comprise 6 to 22 carbons, 8 to 20 carbons, 10 to 18 carbons, or 12 to 16 carbons.

The fatty acid esters can include, for example, sugar fatty acid esters, fatty acid methyl esters (FAME), fatty acid ethyl esters, triglycerides, phospholipids, cholesterol esters and others. In certain preferred embodiments, the fatty acid ester(s) comprise oleic acid, e.g., methyl oleate (oleic acid methyl ester) or ethyl oleate (oleic acid ethyl ester).

Other MEL-like molecules can also be produced according to the subject invention, e.g., mannosyl-mannitol lipids (MML), mannosyl-arabitol lipids (MAL), and/or mannosyl-ribitol lipids (MRL).

In certain embodiments, a plurality of MEL molecules can be recovered from one *M. guilliermondii* culture produced according to the subject methods.

Advantageously, in certain embodiments, the methods lead to production of surprisingly higher yields of MEL and/or MEL-like molecules than are achieved when MEL are produced using known methods (e.g., through cultivation of *Pseudozyma* and/or *Ustilago*), and in less time.

Phase 1

In one embodiment, phase one of the method comprises inoculating an initial nutrient medium with a *Meyerozyma guilliermondii* yeast to produce a yeast culture; and cultivating the yeast culture for 1-7 days, e.g., 2 days, at a temperature and at a pH (i.e., a first temperature and a first pH) favorable for accumulation of yeast cell biomass.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique.

In certain embodiments, the initial nutrient medium comprises a sugar (e.g., glucose) and sources of proteins, amino acids, nitrogen, potassium, phosphorous, magnesium, calcium, sodium, and/or carbon.

In one embodiment, the nitrogen source can be, for example, potassium nitrate, ammonium nitrate ammonium sulfate, ammonium phosphate, ammonia, urea, and/or ammonium chloride. These nitrogen sources may be used independently or in a combination of two or more.

In one embodiment, the carbon source can be carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, coconut oil, canola oil, rapeseed oil, safflower oil, rice bran oil, olive oil, corn oil, sesame oil, and/or linseed oil; etc. These carbon sources may be used independently or in a combination of two or more.

In one embodiment, growth factors and trace nutrients for microorganisms are included in the nutrient medium. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included in the nutrient medium. Usable inorganic salts can be potassium dihydrogen phosphate, dipotassium hydrogen phosphate, disodium hydrogen phosphate, magnesium sulfate, magnesium chloride, iron sulfate (e.g., ferrous sulfate heptahydrate), iron chloride, manganese sulfate, manganese sulfate monohydrate, manganese chloride, zinc sulfate, lead chloride, copper sulfate, calcium chloride, calcium carbonate, and/or sodium carbonate. These inorganic salts may be used independently or in a combination of two or more.

In some embodiments, the microbes are grown in a solid nutrient substrate comprising a plurality of individual solid items, e.g., pieces, morsels, grains or particles, that are, optionally, prepared by mixing with a liquid nutrient medium, salts and/or water. In preferred embodiments, the solid items are foodstuff. The foodstuff can include one or more of, for example, rice, beans, lentils, legumes, oats and oatmeal, corn and other grains, pasta, wheat bran, flours or meals (e.g., corn flour, nixtamilized corn flour, partially hydrolyzed corn meal), and/or other similar foodstuff to provide surface area for the microbial culture to grow and/or feed on.

In preferred embodiments, the solid nutrient substrate serves as a three-dimensional scaffold that provides ample surface area on which microbes can grow. In some embodiments, the methods allow for microbes to grow in the form of a biofilm. In some embodiments, the foodstuff in the matrix can also serve as a source of nutrients for the microbes.

In an exemplary embodiment, the initial nutrient medium of phase one comprises glucose, ammonium nitrate, potassium phosphate, monosodium phosphate, magnesium sulfate heptahydrate, magnesium sulfate monohydrate, and calcium chloride monohydrate. In another exemplary embodiment, one or both of soybean oil and mannose are also included.

The microbial inoculant according to the subject methods preferably comprises cells and/or propagules of the desired microorganism, which can be prepared using any known fermentation method. In some embodiments, the propagules are hyphae or spores. The inoculant can be pre-mixed with water and/or a liquid nutrient medium, if desired.

In one embodiment, seeding the system with the microbial inoculant can be performed by pumping, pouring, sprinkling or spraying the inoculum into the vessel being used for fermentation.

Activation, or germination, of the microbes can be enhanced, at the time of inoculation, during cultivation or at the time of application, by adding L-alanine in low (micromolar) concentrations, manganese or any other known growth enhancer or stimulant.

In some embodiments, the method for cultivation may optionally comprise adding additional acids and/or antimicrobials into the substrate before and/or during phase one and/or phase two of the subject methods.

In one embodiment, the first temperature and the first pH, at which phase one occurs, are favorable for accumulation of yeast biomass. In one embodiment, the first temperature can be about 25° C. to 50° C., or about 26° C. to about 30° C. In one embodiment, the first pH can be about 5.0 to 7.5, or about 5.5 to 7.0, or about 6.0 to 6.5.

The yeast culture can be grown for as long as necessary for the yeast to reach the desired cell biomass, including from 1 day to 1 week, preferably about 2 days (e.g., between 45 and 50 hours).

Phase 2

In one embodiment, phase two of the method comprises altering the initial nutrient medium, first temperature and first pH, and continuing to cultivate the yeast culture for 1 to 7 additional days. In certain embodiments, the alterations in nutrient medium, temperature and pH influence the yeast to produce MEL in the yeast culture.

In one embodiment, altering the initial nutrient medium comprises supplementing the nutrient medium with a sugar alcohol and/or with mannose, and/or comprises replacing the glucose with a source of fatty acids.

In certain embodiments, the sugar alcohol is selected from erythritol, mannitol, arabitol, and ribitol. In preferred embodiments, the sugar alcohol is erythritol.

In certain embodiments, the source of fatty acids is an oil, such as, for example, soybean oil, canola oil, safflower oil, olive oil, corn oil, rapeseed oil, peanut oil, or another vegetable or plant oil. In preferred embodiments, the source of fatty acids is soybean oil.

In one embodiment, the first temperature and the first pH at which the yeasts are cultivated are altered in phase two. In certain embodiments, the first temperature is lowered to a second temperature of about 23° C. to about 25° C., e.g., about 24° C., during phase two. In certain embodiments, the first pH is lowered to a second pH of about 3.0 to about 4.5, e.g., about 3.5 to about 4.0.

In certain embodiments, the first pH naturally lowers during the course of cultivation. Thus, in some embodiments, the method can comprise simply stabilizing the pH upon reaching 3.5 to 4.0.

After continuing to cultivate the yeast culture during phase two of the subject method, for example, for an additional 1 to 7 days, or an additional 1 to 5 days after completion of phase one, MEL production can be observed. In certain embodiments, MEL production is observed after as little as 24 hours after the start of phase two.

According to the subject methods, the MEL growth by-products can be retained in the cells of the microorganisms and/or secreted into the solid substrate and/or liquid medium in which the microbes are growing. In one embodiment, the MEL by-products are produced into the culture, where it separates into a foamy layer at the top of the culture. Advantageously, this stratification allows for improved, safer recovery of the MEL product, compared with solvent extraction methods. In some embodiments, the MEL can be recovered from the culture simply by collecting the foam, and then, if desired, the MEL can be purified according to known methods.

The subject methods can be used to produce high concentrations of MEL, for example, from about 50 g/L to about 500 g/L, about 80 g/L to about 400 g/L, or about 100 g/L to about 300 g/L of MEL.

The methods for cultivation of microorganisms and production of microbial by-products can be performed in a batch process or a continuous/quasi-continuous process.

In one embodiment, all of the culture is removed upon completion of the cultivation (e.g., upon, for example, achieving a desired cell density, or concentration of MEL). In this batch procedure, an entirely new batch is initiated after sterilization of the fermentation system.

In another embodiment, only a portion of the culture is removed at any one time. In this manner, a continuous or quasi-continuous system is created.

Microorganisms

The microorganisms according to the subject invention can be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the microorganism is yeast or fungus. In one embodiment, the yeast or fungus is a *Pichia* yeast, such as, for example, *P. guilliermondii, P. anomala, P. kudriavzevii*, and *P. occidentalis*. In a preferred embodiment, the yeast is *Pichia guilliermondii*, also known as *Meyerozyma guilliermondii*.

Preparation of Microbe-Based Products

In certain embodiments, the subject invention provides microbe-based products, as well as their uses in a variety of settings including, for example, oil and gas production; bioremediation and mining; waste disposal and treatment; animal health (e.g., livestock production and aquaculture); plant health and productivity (e.g., agriculture, horticulture, crops, pest control, forestry, turf management, and pastures); and human health (e.g., probiotics, pharmaceuticals and cosmetics).

One microbe-based product of the subject invention is simply a yeast culture comprising cells of a MEL-producing yeast, a nutrient medium, and a high concentration of MEL. The MEL can be retained in the cells of the yeast and/or present as a secretion in the nutrient medium. The yeast culture can also comprise other metabolites produced by the yeast.

The product of fermentation may be used directly without extraction or purification. If desired, extraction and purification can be easily achieved. In some embodiments, extraction does not require solvents. In some embodiments, standard extraction methods or techniques known to those skilled in the art, including those that use solvents, can be employed.

In some embodiments, all or a portion of the entire culture, including the MEL, can be harvested from the vessel and then processed to recover the MEL. For example, in some embodiments, the culture is centrifuged to remove the yeast cells and then subjected to known extraction and, optionally, purification methods to recover the MEL. All or a portion of the product can also be dried and later dissolved in water.

In a specific preferred embodiment, the composition comprises MEL, which include MEL isomers, modified MEL molecules, and/or MEL-like molecules.

In some embodiments, the yeast culture can comprise high concentrations of MEL, for example, about 10 ppm to about 10,000 ppm of MEL, about 100 ppm to about 5,000 ppm, about 200 to about 1,000 ppm, about 300 ppm to about 800 ppm, or about 500 ppm.

In some embodiments, the yeast culture can comprise high concentrations of MEL, for example, about 50 g/L to about 500 g/L, about 80 g/L to about 400 g/L, or about 100 g/L to about 300 g/L of MEL.

Advantageously, in accordance with the subject invention, the microbe-based product may comprise the substrate in which the microbes were grown. In one embodiment, the composition may be, for example, at least 1%, 5%, 10%, 25%, 50%, 75%, or 100%, by weight, growth medium. The amount of biomass in the composition, by weight, may be, for example, anywhere from 0 to 100%, about 10 to 90%, or about 20 to 75%.

If present in the microbe-based product, the microorganisms may be in an active or inactive form. In some embodiments, the microorganisms are in hyphae or mycelial form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

In one embodiment, the composition does not comprise living microorganisms. In one embodiment, the composition does not comprise microorganisms, whether living or inactive.

In one embodiment, the compositions comprise one or more microbial growth by-products, wherein the growth by-product has been extracted from the culture and, optionally, purified. For example, in one embodiment, the composition comprises a foamy MEL layer that forms during cultivation, which can be extracted and then subjected to known purification methods.

In certain embodiments, the compositions according to the subject invention can have advantages over, for example, purified microbial metabolites alone, due to, for example, the use of the entire culture. When producing yeasts, for example, the composition can comprise high concentrations of mannoprotein as a part of yeast cell wall's outer surface (mannoprotein is a highly effective bioemulsifier). Additionally, the compositions can comprise a variety of microbial metabolites (e.g., biosurfactants, enzymes, acids, solvents, and other) in the culture that may work in synergy with one another to achieve a desired effect.

In some embodiments, the products include other microbial growth by-products, in addition to the MEL, including, for example, other biosurfactants, enzymes and/or metabolites.

In one embodiment, the composition comprises other biosurfactants. These other biosurfactants can be glycolipids and/or glycolipid-like biosurfactants, such as, for example, rhamnolipids (RLP), sophorolipids (SLP), and/or trehalose lipids. In one embodiment, the biosurfactants comprise lipopeptides and/or lipopeptide-like biosurfactants, such as, e.g., surfactin, iturin, fengycin, athrofactin, viscosin and/or lichenysin. In one embodiment, the biosurfactants comprise polymeric biosurfactants, such as, for example, emulsan, lipomanan, alasan, and/or liposan.

In some embodiments, the composition can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

The microbe-based product can be removed from the container and transferred to the site of application via, for example, tanker, for immediate use.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Methods of Use

The compositions of the subject invention can be used for a variety of purposes. In one embodiment, the composition can be used in agriculture. For example, methods are provided wherein a composition produced according to the subject invention is applied to a plant and/or its environment to treat and/or prevent the spread of pests and/or diseases. The composition can also be useful for enhancing water dispersal and absorption in the soil, as well as to enhance nutrient absorption from the soil through plant roots, facilitate plant health, increase yields, and manage soil aeration.

In one embodiment, the subject compositions can be highly advantageous in the context of the oil and gas industry. When applied to an oil well, wellbore, subterranean formation, or to equipment used for recovery oil and/or gas, the compositions produced according to the subject invention can be used in methods for enhancement of crude oil recovery; reduction of oil viscosity; removal and dispersal of paraffin from rods, tubing, liners, and pumps; prevention of equipment corrosion; recovery of oil from oil sands and stripper wells; enhancement of fracking operations as fracturing fluids; reduction of $H_2S$ concentration in formations and crude oil; and cleaning of tanks, flowlines and pipelines.

In one embodiment, the compositions produced according to the subject invention can be used to improve one or more properties of oil. For example, methods are provided wherein the composition is applied to oil or to an oil-bearing formation in order to reduce the viscosity of the oil, convert the oil from sour to sweet oil, and/or to upgrade the oil from heavy crude into lighter fractions.

In one embodiment, the compositions produced according to the subject invention can be used to clean industrial equipment. For example, methods are provided wherein the composition is applied to oil production equipment such as an oil well rod, tubing and/or casing, to remove heavy hydrocarbons, paraffins, asphaltenes, scales and other contaminants from the equipment. The composition can also be applied to equipment used in other industries, for example, food processing and preparation, agriculture, paper milling, and others where fats, oils and greases build up and contaminate and/or foul the equipment.

In one embodiment, the compositions produced according to the subject invention can be used to enhance animal health. For example, methods are provided wherein the composition can be applied to animal feed or water, or mixed with the feed or water, and used to prevent the spread of disease in livestock and aquaculture operations, reduce the need for antibiotic use in large quantities, as well as to provide supplemental proteins and other nutrients.

In one embodiment, the compositions produced according to the subject invention can be used to prevent spoilage of food, prolong the consumable life of food, and/or to prevent food-borne illnesses. For example, methods are provided wherein the composition is applied to a food product, such as fresh produce, baked goods, meats, and post-harvest grains, to prevent undesirable microbial growth.

Other uses for the subject compositions include, but are not limited to, biofertilizers, biopesticides, bioleaching, bioremediation of soil and water, pharmaceutical adjuvants (for increasing bioavailability of orally ingested drugs), cosmetic products, control of unwanted microbial growth, and many others.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used. For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used, for example, within 300 miles, 200 miles, or even within 100 miles. Advantageously, this allows for the compositions to be tailored for use at a specified location. The formula and potency of microbe-based compositions can be customized for a specific application and in accordance with the local conditions at the time of application.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention.

Example 1—Production of MEL Using *M. guilliermondii*

*M. guilliermondii* was cultivated using submerged cultivation in a culture medium comprising:
2 g/L Glucose
1 g/L Yeast Extract
1 g/L NH4NO3
2.5 g/L K2HPO4
0.15 g/L NaH2PO4
0.5 g/L MgSO4*7H2O
0.1 g/L CaCl2*H2O
0.02 g/L MgSO4*H2O
100 ml/L Soybean oil Initially, pH was set to 6.0 and temperature was set to 26° C. After 2 days, when biomass accumulation had occurred, the temperature was lowered to 24° C. Erythritol (40 g/L) was added to the culture. pH was allowed to decrease to about 3.5 to 4.0 during cultivation.

MEL were produced within 3 to 7 days after the start of biomass accumulation, with a maximum concentration obtained at day 7. The MEL concentrated in a foamy layer at the top of the culture.

MEL concentrations produced were compared to MEL production by *P. aphidis* after 14 days. Rough analysis of MEL produced by *M. guilliermondii* at day 3, 6 and 7 showed that the amount of MEL produced was greater than the observed amount of MEL produced by 14 day culture of *P. aphidis*.

Example 2—Characteristics of Purified Mel from *M. guilliermondii*

Figure 1B:
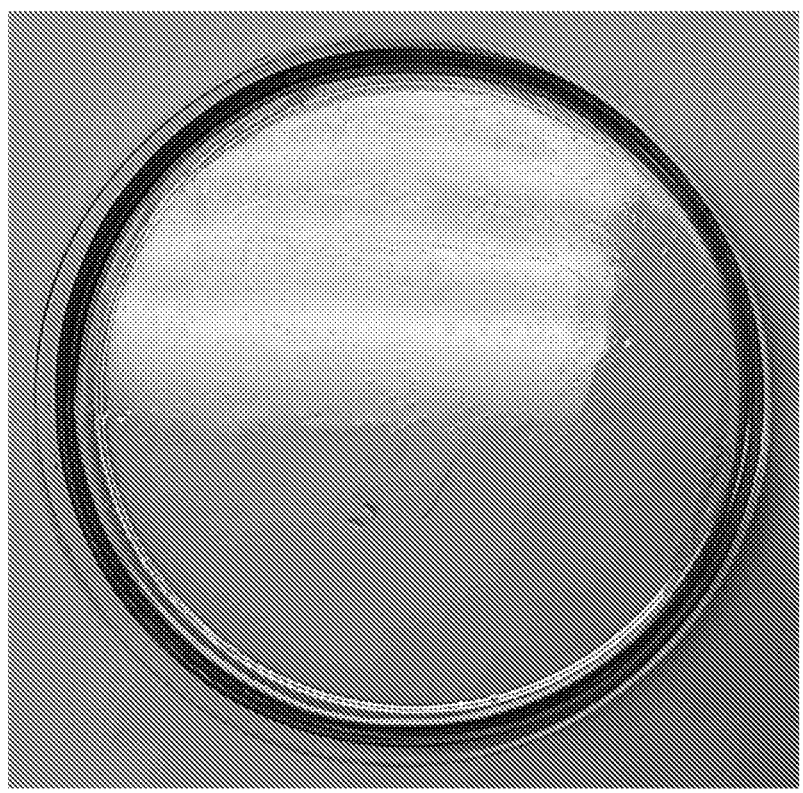

The MEL produced according to Example 1 above were tested for surface tension reduction capability. FIGS. 1A-1B show the results of oil displacement testing in petri dishes before (1A) and after (1B) treatment. Testing of different concentrations of the MEL after purification provided the following surface tension measurements:
100% purified MEL: 32 mN;
10% purified MEL: 32 mN;
1% purified MEL: 33 mN;
0.1% purified MEL: 35 mN;
0.01% purified MEL: 37 mN;
0.001% purified MEL: 46 mN.

Example 3—HPLC Ms Analysis of *M. guilliermondii* Culture

Analysis of *M. guilliermondii* cultures was performed on Shimadzu Nexera X2 UHPLC fitted with a Thermo Scientific™ Acclaim™ Surfactant Column coupled with a Shimadzu LCMS 8040.

Figure 2A:
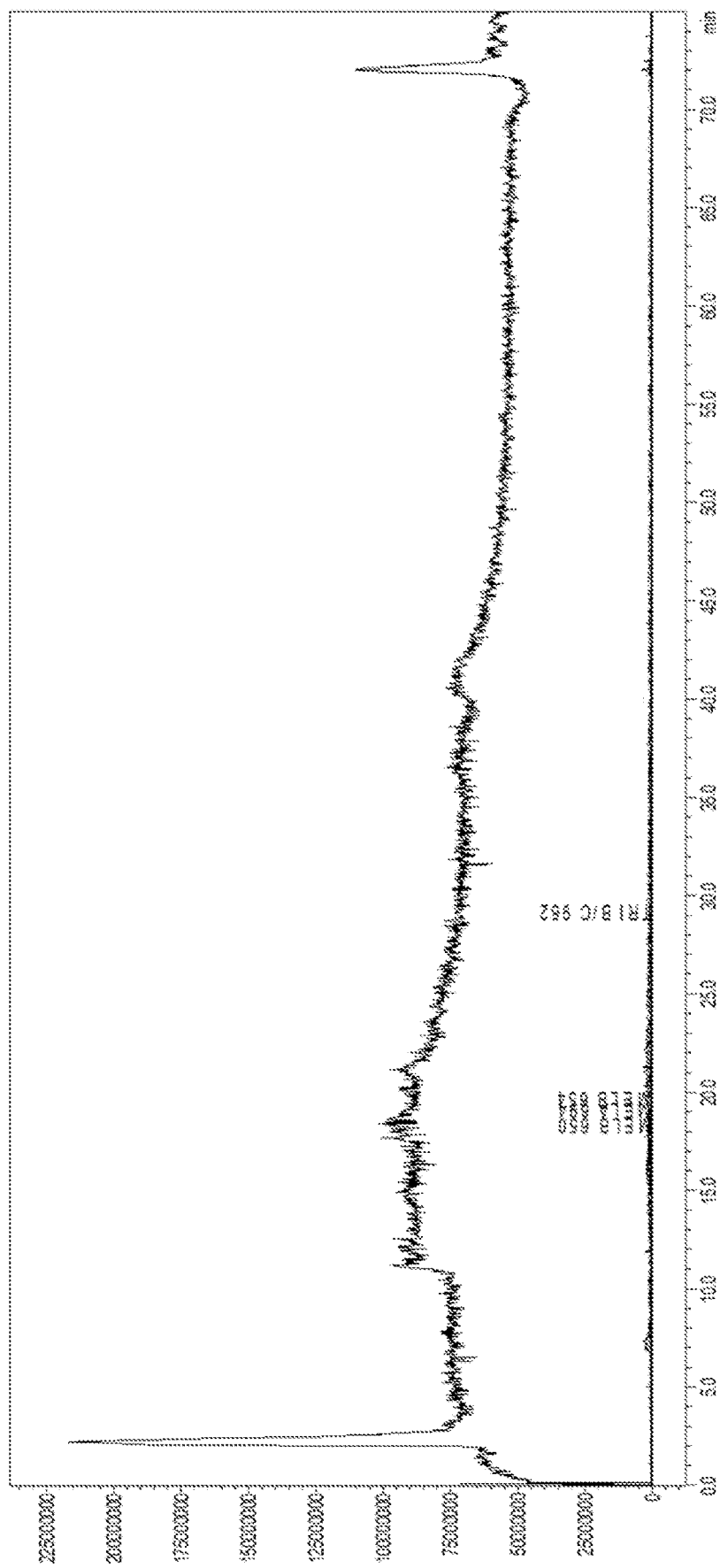
FIGS. 2A-2B show the results of HPLC MS analysis of *M. guilliermondii* culture at day 3 of cultivation. 2A shows the full chromatogram results, and 2B shows a zoomed-in view of the MEL types identified.
Figure 2B:
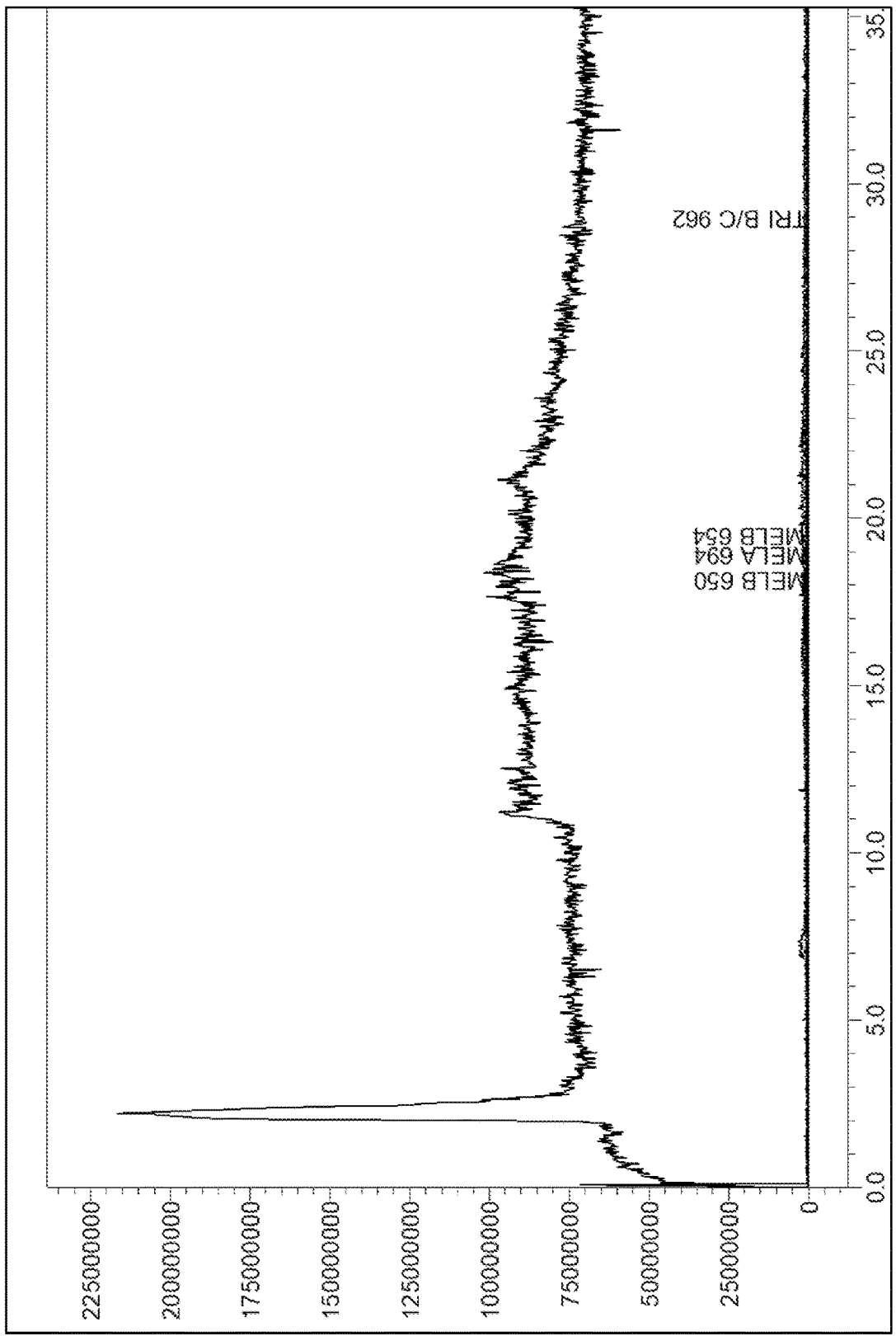
Figure 3A:
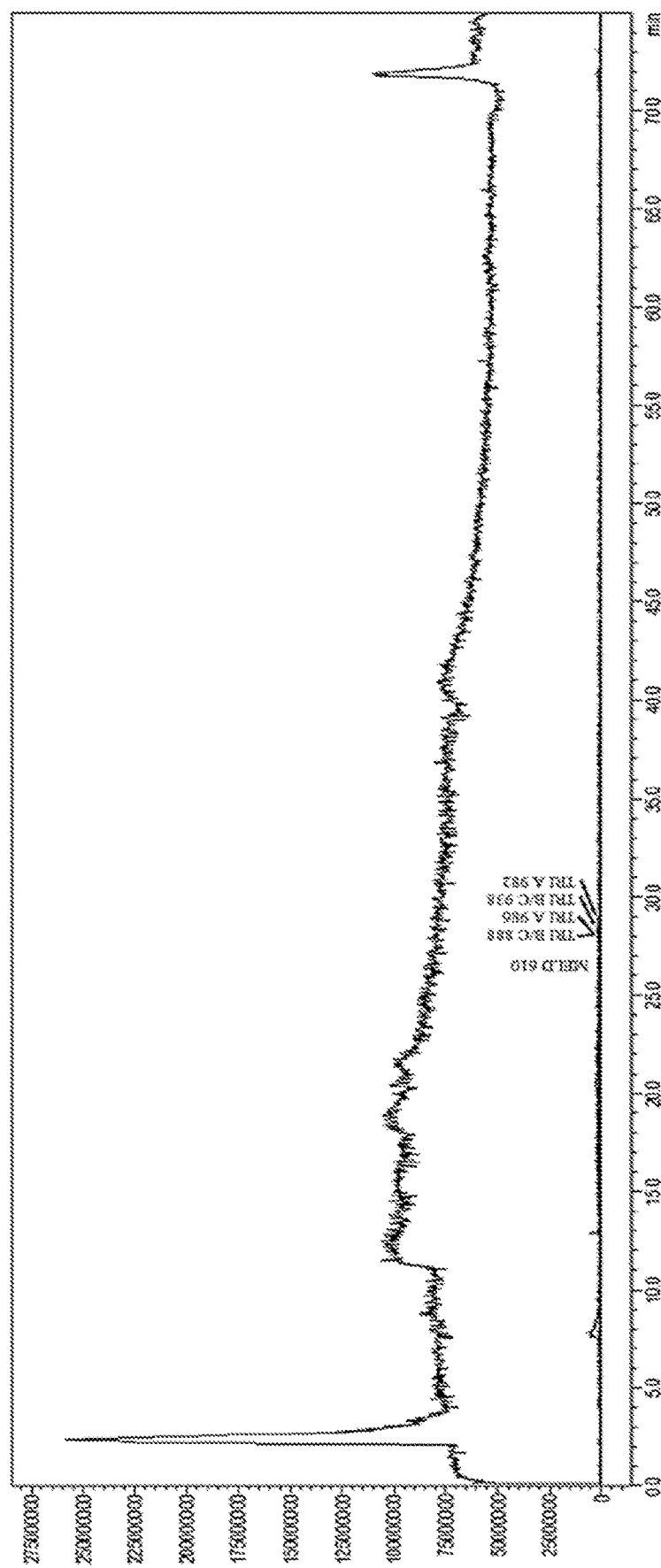
FIGS. 3A-3B show the results of HPLC MS analysis of *M. guilliermondii* culture at day 6 of cultivation. 3A shows the full chromatogram results, and 3B shows a zoomed-in view of the MEL types identified.
Figure 3B:
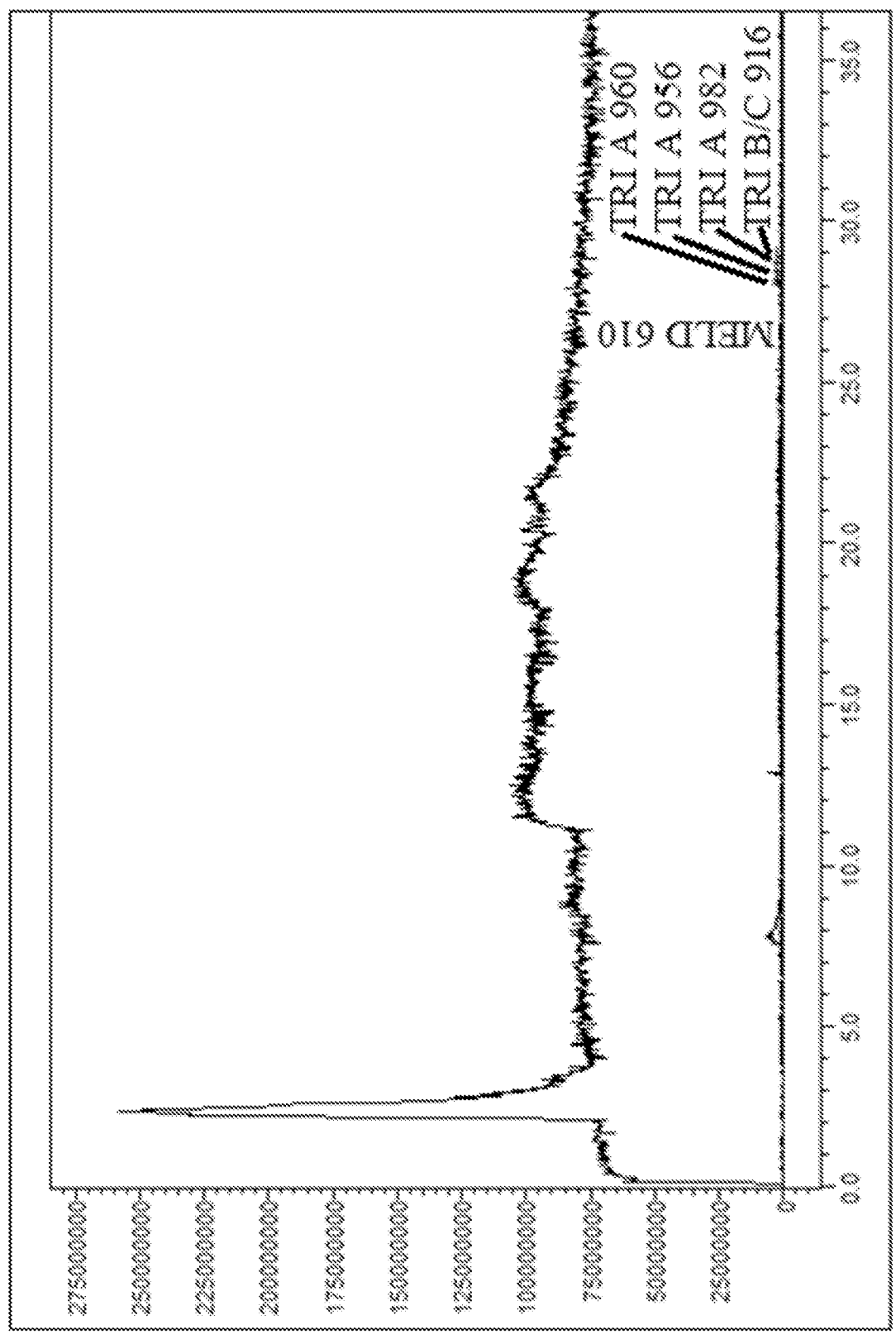
Figure 4A:
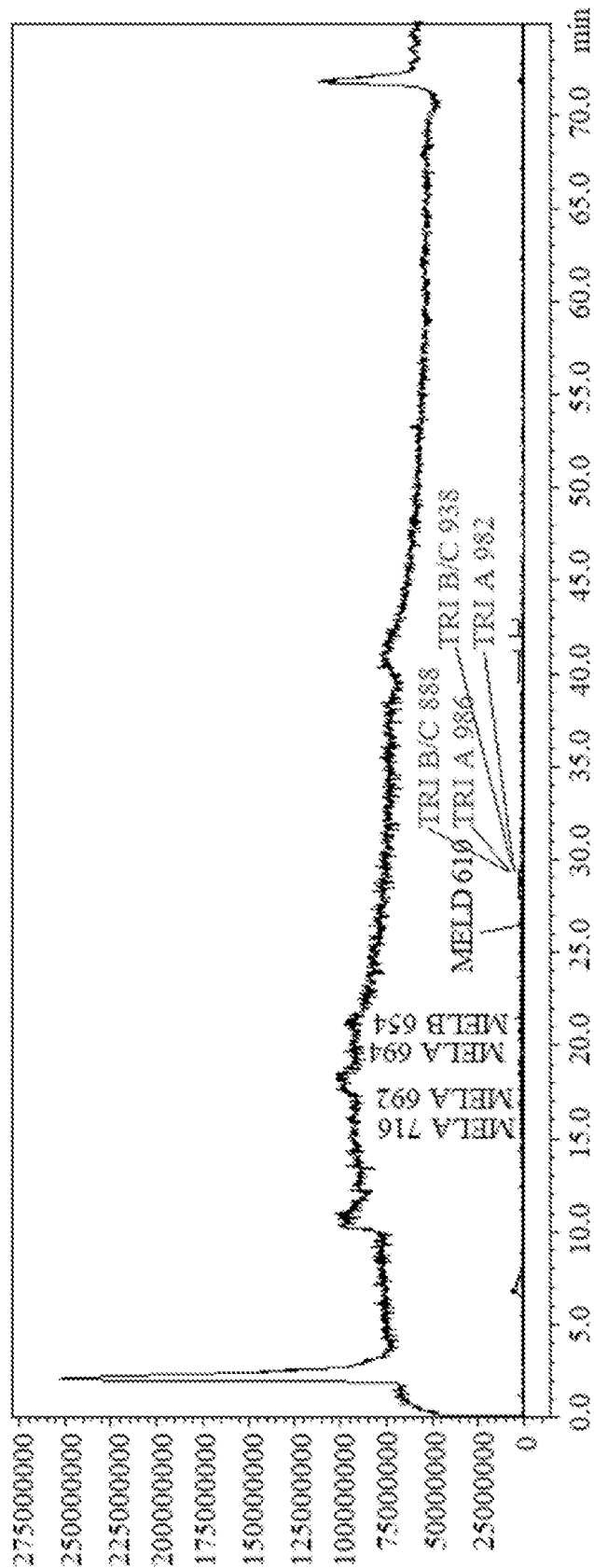
FIGS. 4A-4B show the results of HPLC MS analysis of *M. guilliermondii* culture at day 7 of cultivation. 4A shows the full chromatogram results, and 4B shows a zoomed-in view of the MEL types identified.
Figure 4B:
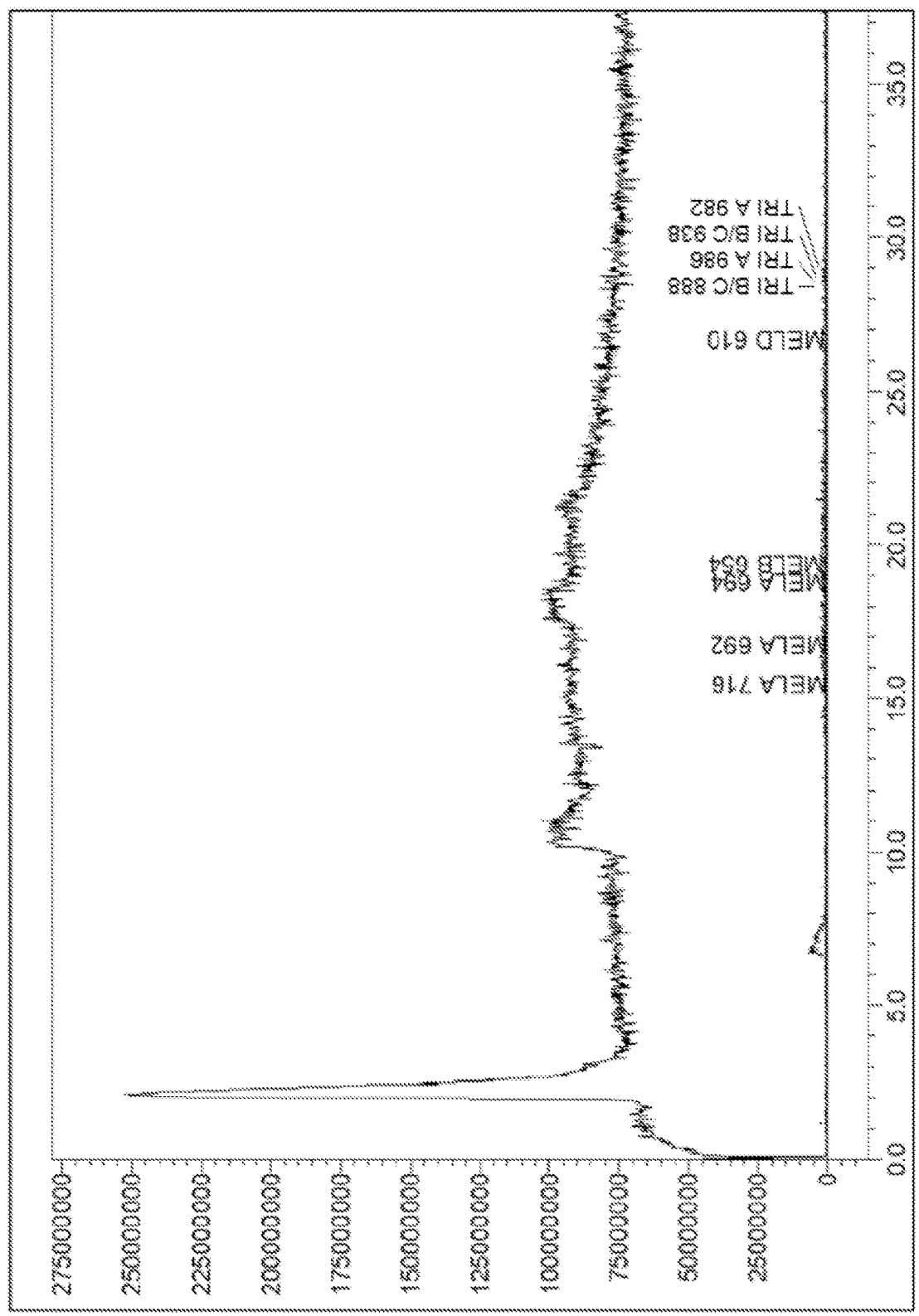

In the post run analysis, an ion trace was performed, looking for 93 different isomers of MEL. Referring to FIGS. 2-4, chromatograms indicated the identity and distribution of MEL isomers at day 3 (2A-2B), day 6 (3A-3B), and day 7 (4A-4B) of total cultivation.

The MEL peaks appear very small on the chromatogram, as the samples comprised a whole culture prior to extraction and/or concentration. The greatest concentration of MEL was observed after 7 days of cultivation.

Tables 1-3 below indicate numerical values for chromatogram results. The Area % value indicates the ratio of the MEL isomer group in comparison to the area of all MEL peaks.

TABLE 1

Chromatogram results for whole culture after 3 days of cultivation

| Type | Area | Area % |
| --- | --- | --- |
| MEL A | 4,451,122 | 12% |
| MEL B | 5,546,805 | 15% |
| MEL D | 14,886,834 | 40% |
| TRI A | 5,305,540 | 14% |
| TRI B/C | 7,264,885 | 19% |
| Total Area | 37,455,186 | |

TABLE 2

Chromatogram results for whole culture after 6 days of cultivation

| Type | Area | Area % |
| --- | --- | --- |
| MEL A | 6,632,602 | 17% |
| MEL B | 7,393,183 | 19% |
| MEL D | 10,417,591 | 27% |
| TRI A | 6,661,589 | 17% |
| TRI B/C | 7,819,794 | 20% |
| Total Area | 38,924,759 | |

TABLE 3

Chromatogram results for whole culture after 7 days of cultivation

| Type | Area | Area % |
| --- | --- | --- |
| MEL A | 3,287,457 | 8% |
| MEL B | 9,904,760 | 23% |
| MEL D | 16,098,621 | 38% |
| TRI A | 4,568,914 | 11% |
| TRI B/C | 8,369,963 | 20% |
| Total Area | 42,229,715 | |

REFERENCES

Arutchelvi, J. I., Bhaduri, S., Uppara, P. V., & Doble, M. (2008). Mannosylerythritol lipids: a review. J. Ind. Microb. & Biotech., (12), 1559.

We claim:

1. A method for producing a mannosylerythritol lipid (MEL), the method comprising:
  a) inoculating an initial nutrient medium with a *Meyerozyma guilliermondii* yeast to produce a yeast culture comprising yeast cells and medium;
  b) cultivating the yeast culture at a first temperature and a first pH favorable for accumulation of yeast cell biomass;
  c) altering the initial nutrient medium, the first cultivation temperature and the first cultivation pH; and
  d) continuing to cultivate the yeast culture, wherein the alterations in nutrient medium, temperature and pH influence the yeast to produce the MEL in the yeast culture;
  wherein the initial nutrient medium comprises glucose and sources of proteins, amino acids, nitrogen, potassium, phosphorous, magnesium, calcium, sodium, and/or carbon;
  wherein said first temperature is about 25° C. to 30° C. and said first pH is about 5.5 to 7.0; and wherein c) comprises:
    supplementing the nutrient medium with a sugar alcohol and/or mannose,
    replacing the glucose with a source of fatty acids,
    lowering the first cultivation temperature to a second temperature of about 23° C. to 25° C., and
    lowering the first pH to a second pH of about 3.5 to 4.0.

2. The method of claim 1, wherein cultivation of the yeast culture in b) is performed for 1 to 7 days.

3. The method of claim 1, wherein the continued cultivation of the yeast culture in d) is performed for 1 to 7 days.

4. The method of claim 1, wherein the initial nutrient medium comprises glucose, ammonium nitrate, potassium phosphate, monosodium phosphate, magnesium sulfate heptahydrate, magnesium sulfate monohydrate, calcium chloride monohydrate, and, optionally, one or both of soybean oil and mannose.

5. The method of claim 1, wherein the sugar alcohol is selected from the group consisting of erythritol, mannitol, arabitol, and ribitol.

6. The method of claim 5, wherein the sugar alcohol is erythritol.

7. The method of claim 1, wherein the source of fatty acids is one or more of soybean oil, canola oil, safflower oil, olive oil, corn oil, rapeseed oil, peanut oil, or another vegetable or plant-based oil.

8. The method of claim 1, wherein the source of fatty acids is soybean oil.

9. The method of claim 1, wherein the yeast produces MEL in the yeast culture in the form of a foamy layer on top of the medium.

10. The method of claim 1, further comprising extracting the MEL from the yeast culture and, optionally, purifying the MEL.

11. The method of claim 1, wherein the MEL comprises one or more of a MEL molecule and/or an isomer thereof, and/or a MEL-like molecule.

12. The method of claim 11, wherein the MEL molecule and/or isomer thereof is a MEL A (di-acetylated), MEL B (mono-acetylated at C4), MEL C (mono-acetylated at C6), MEL D (non-acetylated), tri-acetylated MEL A, and/or tri-acetylated MEL B/C.

13. The method of claim 11, wherein the MEL-like molecule is an oleic acid ethyl ester, a mannosyl-mannitol lipid (MML), a mannosyl-arabitol lipid (MAL), or a mannosyl-ribitol lipid (MRL).

* * * * *